US007744588B2

(12) United States Patent
Nash et al.

(10) Patent No.: US 7,744,588 B2
(45) Date of Patent: *Jun. 29, 2010

(54) TOOL FOR FACILITATING THE CONNECTING OF A CATHETER OR OTHER TUBULAR MEMBER ONTO A GUIDE-WIRE WITHOUT ACCESS TO THE ENDS OF THE GUIDE WIRE

(75) Inventors: John E. Nash, Chester Springs, PA (US); Gregory Walters, Malvern, PA (US); Douglas G. Evans, Downingtown, PA (US); David Szabo, Trappe, PA (US); Michael Paris, Hatfield, PA (US)

(73) Assignee: Kensey Nash Corporation, Exton, PA (US)

( * ) Notice: Subject to any disclaimer, the term of this patent is extended or adjusted under 35 U.S.C. 154(b) by 1575 days.

This patent is subject to a terminal disclaimer.

(21) Appl. No.: 10/477,475

(22) PCT Filed: May 21, 2002

(86) PCT No.: PCT/US02/16251

§ 371 (c)(1),
(2), (4) Date: Feb. 27, 2004

(87) PCT Pub. No.: WO02/094364

PCT Pub. Date: Nov. 28, 2002

(65) Prior Publication Data

US 2004/0133185 A1 Jul. 8, 2004

(51) Int. Cl.
*A61M 25/16* (2006.01)
(52) U.S. Cl. .................................... 604/533

(58) Field of Classification Search .................. 604/528, 604/30, 103, 164.01, 164.02, 236, 247, 533; 600/567; 606/185, 213; 623/1.11; 116/234
See application file for complete search history.

(56) References Cited

U.S. PATENT DOCUMENTS 5,046,497 A * 9/1991 Millar .................... 600/309

(Continued)

FOREIGN PATENT DOCUMENTS

CA 2184502 3/1997

(Continued)

OTHER PUBLICATIONS

Canadian Office Action dated Feb. 23, 2007 for corresponding Application No. 2,447,621.

(Continued)

*Primary Examiner*—Nicholas D Lucchesi
*Assistant Examiner*—Victoria P Campbell
(74) *Attorney, Agent, or Firm*—Caesar, Rivise, Bernstein, Cohen & Pokotilow, Ltd.

(57) ABSTRACT

An attachment tool to facilitate the attachment of one or more catheters or similar elongated instruments to a guide-wire or other elongated guide member, without requiring access to either end of said wire or member. The tool provides repeatable and reliable alignment of components to be attached, while being operated with a single hand. The catheter systems can be used for revascularization or treatment of arteries and lumens within the body, and the associated delivery of therapies therein and can include side attachable and over-the-wire components and/or low profile combination catheters to allow for flush and extraction of debris in small or tortuous anatomic pathways.

26 Claims, 8 Drawing Sheets

U.S. PATENT DOCUMENTS

| | | | |
|---|---|---|---|
| 5,131,407 A | 7/1992 | Ischinger et al. | |
| 5,344,413 A | 9/1994 | Allman et al. | |
| 5,776,115 A * | 7/1998 | Antoshkiw et al. | 604/524 |
| 5,879,361 A * | 3/1999 | Nash | 606/159 |
| 6,022,336 A | 2/2000 | Zadno-Azizi et al. | |
| 6,190,333 B1 | 2/2001 | Valencia | |
| 6,517,518 B2 * | 2/2003 | Nash et al. | 604/164.02 |
| 6,569,151 B1 * | 5/2003 | Nash et al. | 604/533 |
| 6,872,192 B2 * | 3/2005 | Nash et al. | 604/164.02 |

FOREIGN PATENT DOCUMENTS

| | | |
|---|---|---|
| EP | 0328760 A2 | 8/1989 |
| EP | 0348136 A2 | 12/1989 |

OTHER PUBLICATIONS

International Search Report for PCT/US 02/16251 mailed Jun. 5, 2003.

International Search Report for PCT/US02/16251 mailed May 6, 2003.

* cited by examiner

TOOL FOR FACILITATING THE CONNECTING OF A CATHETER OR OTHER TUBULAR MEMBER ONTO A GUIDE-WIRE WITHOUT ACCESS TO THE ENDS OF THE GUIDE WIRE

FIELD OF THE INVENTION

This invention relates generally to medical devices and more particularly to devices for use with catheters or other tubular devices that are arranged to be located at some intralumenal, e.g., intra-vascular, position within the body of a being by a conventional guide-wire or other guide member.

BACKGROUND OF THE INVENTION

Heretofore the mounting of a tubular instrument, e.g., a catheter, on a guide-wire has typically required access to either the distal or the proximal end of the guide-wire. Where the guide-wire is already in place, access has been achieved by mounting the instrument on the proximal end of the guide-wire and then sliding it into place over or along the guide-wire. For example, the so-called "over-the-wire" catheter (such as a balloon angioplasty catheter) has a central or other longitudinal extending passageway therethrough arranged to receive the guide-wire. In particular, the passageway of such a catheter is introduced on the proximal end of the guide-wire and then the catheter is slid down the guide-wire to the desired location. The advantage of this type of instrument and guidance system is that it can have a relatively small cross-sectional area or "crossing-diameter," a feature of some importance in applications wherein the lumen being traversed is small, e.g., an artery occluded by atherosclerotic deposits. The so-called "mono-rail" catheter doesn☐t make use of a central passageway for receipt of the guide-wire, but instead makes use of some externally located connector located on the distal end of the catheter and arranged to receive the guide-wire through it. The mono-rail catheter is also arranged to be introduced on the proximal end of the guide-wire, but outside the guide-wire so that the guide-wire passes through the connector on the distal end of the catheter, with the catheter itself being located beside the guide-wire so that it can be slid along the guide-wire to the desired location.

As will be appreciated by those skilled in the art, if the proximal end of the guide-wire has some structure permanently or transiently mounted or secured on it, e.g., a twist or torque handle (for rotating the guide-wire to a desired angular orientation), a valve (to enable some fluid to be introduced through the guide-wire, such as to inflate a balloon on the distal end of the guide-wire), another catheter, etc., that is of a relatively large diameter or cross-sectional area, such a proximally mounted structure would necessarily impede the mounting of the instrument over the guide-wire once the guide-wire is in place within the being?s body.

In U.S. Pat. No. 6,022,336 (Zadno-Azizi et al.) there is disclosed a catheter system for revascularizing an occluded vessel and for containing any emboli produced during the use of the system. As best seen in FIGS. 7 and 10A of that patent the instrument makes use of plural catheters for providing at least one pair of paths for irrigation and aspiration fluid flow. One of the catheters, designated as an "intermediate" catheter includes an externally mounted lumen structure for receipt of an inner catheter therethrough. This lumen structure may include a longitudinally extending slit or weakened area along the entire length of the lumen structure to facilitate faster and easier insertion and removal of the inner catheter through the side wall of the lumen structure. By inserting and removing the inner catheter through the slit in the side wall of the lumen structure, the need to remove adapters and attachments from the proximal end prior to slidably advancing or removing the intermediate catheter over the inner catheter is eliminated. Thus, this lumen structure which is mounted at the distal end of the intermediate catheter for accommodating the inner catheter enables the intermediate catheter to be guided along the inner catheter in a manner like the heretofore discussed mono-rail catheters are slid along a guide-wire. However, unlike the prior art devices for mounting an instrument on a guide-wire in a mono-rail like arrangement, the device of Zadno-Azizi et al. patent does not require access to the proximal end of the intermediate catheter or guide-wire. Instead the device of the Zadno-Azizi et al. patent enables the inner catheter to be inserted laterally into a longitudinally extending access slit in the lumen structure at a intermediate location along the inner catheter. By inserting and removing the inner catheter through the slit in the side wall of the lumen structure on the distal end of the intermediate catheter, the need to remove adapters and attachments from the proximal end of the intermediate catheter prior to slidably advancing or removing that catheter over the inner catheter is eliminated.

While the instrument of the Zadno-Azizi et al. patent appears generally suitable for its intended purposes, it appears to leave something to be desired from various standpoints. For example, since the lumen structure with the access slit is located externally to the intermediate catheter it will necessarily add its diameter to the diameter of the intermediate catheter, thereby limiting its usefulness to relatively large crossing diameter lumens. Also, the manner in which the intermediate catheter is attached or mounted onto the inner catheter or guide-wire may be somewhat difficult to achieve, and the additional structure, e.g., the slit bearing lumen structure, on the distal end could cause the distal end to get snagged on stents placed in the vessel. Further still, since the slit through which the inner catheter or guide-wire is inserted is linear and extends longitudinally, the inner catheter or guide-wire may come out of the lumen during the traversal of difficult anatomical orientations, e.g,. tortuous vascular paths.

SUMMARY OF THE INVENTION

In accordance with one aspect of the invention, an attachment tool and method of use are provided for facilitating the attachment of a catheter or elongated instrument having a connector thereon to a guide-wire or other elongated guide member. The tool comprises surfaces arranged to cause the catheter to contact the guide-wire or other elongated guide member upon the application of a force, e.g., a twisting force, a longitudinal force, a lateral force, etc., to the tool or to the catheter or elongated instrument, whereupon the catheter or elongated instrument is attached to the guide-wire or other elongated guide member.

In accordance with another aspect of the invention, a tubular instrument system is provided. The system is arranged to be used with a guide-wire or other elongated guide member. The guide-wire or other guide member has a distal end portion arranged to be extended to some interior position within a lumen in the body of a living being, and also has a proximal end portion arranged to be located outside the body of the being. The system comprises at least a first and a second tubular component. The first tubular component has an end portion having a connector arranged to be connected to the guide-wire or other guide member so that the first tubular component can be guided to a desired position within the body of the being.

In accordance with another aspect of the invention the connector establishes a path into which a portion of the guide-wire or other guide member can be inserted from a lateral direction by a twisting action without requiring access to either end of the guide-wire or other guide member.

In accordance with another aspect of the invention, the second tubular component comprises a second end portion including a connector arranged to be readily connected to the guide-wire or other guide member so that the second tubular component can be guided to a desired position within the body of the being along the guide-wire or other guide member.

In accordance with another aspect of the invention the second connector establishes a path into which a portion of the guide-wire or other guide member can be inserted from a lateral direction by a twisting action without requiring access to either end of the guide-wire or other guide member.

In accordance with another aspect of the invention the first tubular component is arranged to have a fluid injected through it at a first flow rate, and in certain of these embodiments, the second tubular component is arranged to evacuate fluids and debris therethrough at a second flow rate. The second flow rate may be higher or the same as the first flow rate. The fluids may contain drugs or other therapy agents, and the extracted fluid may also contain debris created or dislodged by the procedure.

In accordance with another aspect of the invention the second tubular component is arranged to be used in an over-the-guide-wire insertion procedure.

In accordance with another aspect of the invention a combination catheter embodiment is provided including first and second tubular components. The second tubular component is attached adjacent to the first tubular component and has a path or opening at an end portion into which at least a portion of the fluid and debris may enter. The fluid and debris is removed through a channel or passageway in the second tubular component.

In accordance with another aspect of the invention, the first tubular component of the combination catheter includes a connector, like those described above, for attachment to the guide-wire or other guide member. Alternate embodiments may use the traditional over-the-wire approaches to insertion and navigation.

DETAILED DESCRIPTION OF THE PREFERRED EMBODIMENTS

Figure 1:
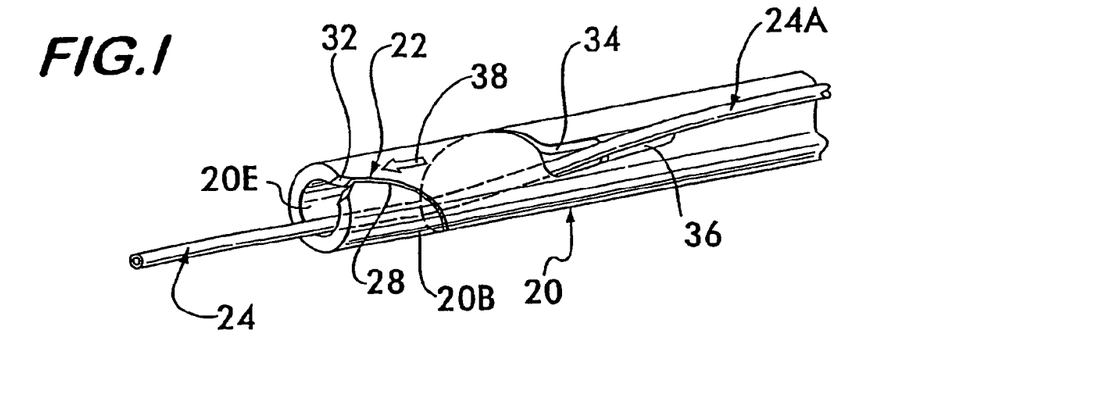
FIG. 1 is an isometric view of the distal end of one embodiment of a catheter constructed in accordance with this invention and shown after it has been mounted on a conventional guide-wire by a helical connector forming a portion of the distal end of the catheter.

Referring now to the various figures of the drawing wherein like reference characters refer to like parts, there is shown at 20 in FIG. 1 the distal end of a tubular instrument, such as an infusate catheter for use in a intravascular revascularization system, and having a connector 22 constructed in accordance with one embodiment of this invention for quickly and easily securing the catheter 20 onto a conventional guide-wire 24 without requiring access to either end of the guide-wire.

Before discussing the details of the connector 22, it should be pointed out that the subject invention can be used with any type of tubular instrument, be it a catheter or otherwise, that is arranged to be extended along a guide-wire or other elongated guide member into the body of a living being to a desired location and without requiring access to either end of the guide-wire or other elongated guide member. In the embodiments shown herein the guide-wire 24 is shown as being a tubular member, but can, if desired be a solid wire.

Figure 7:
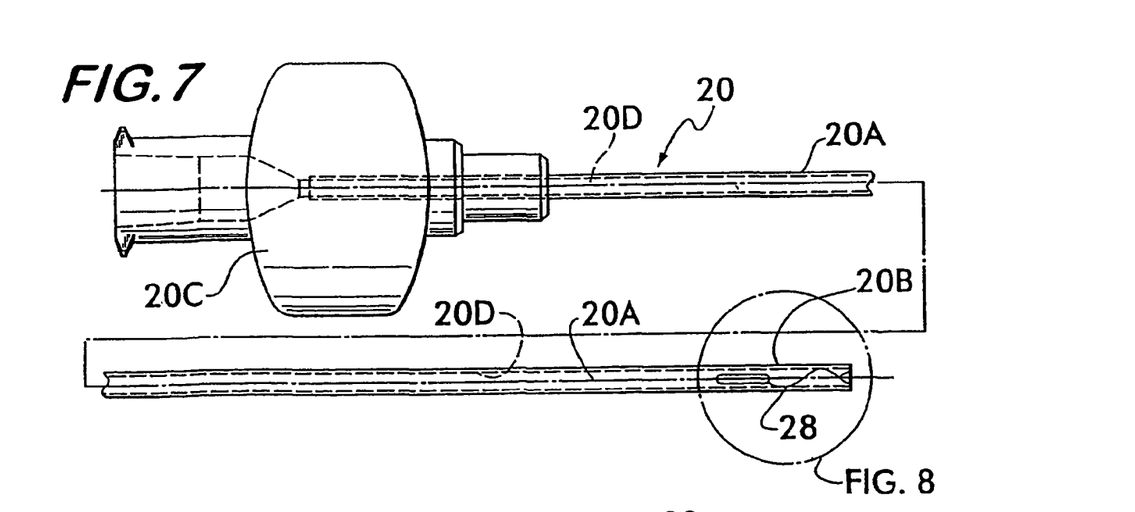
FIG. 7 is a reduced top plan view of the embodiment of the catheter shown in FIG. 1.
Figure 8:
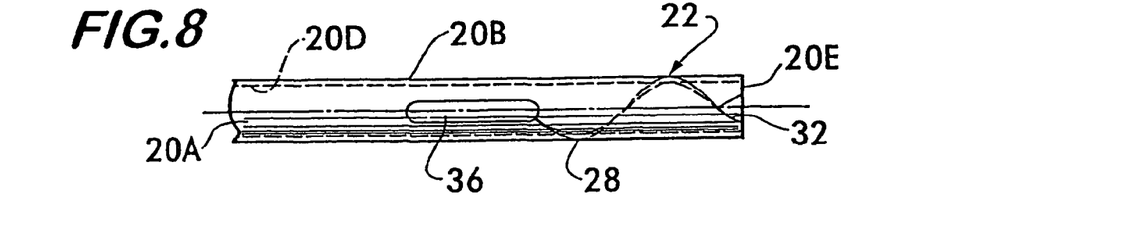
FIG. 8 is an enlarged top plan view of the portion of the embodiment of the catheter shown within the area bounded by the circular broken line in FIG. 7.

The infusate catheter whose distal end is shown in FIG. 1 is shown fully in the plan view of FIG. 7 and is merely exemplary of any type of catheter or tubular instrument for which the subject invention has application and utility (e.g., an angiographic or other diagnostic catheter, a drug or therapy delivery catheter, a prosthesis delivery catheter, a revascularization catheter, a ultrasound or vascular filter wire). As best seen in FIG. 7 the catheter 20 basically comprises an elongated tubular body 20A terminating at a distal end 20B at which the connector 22 of the subject invention is located. The opposite or proximal end of the catheter 22 is in the form of an enlarged hub or connector 20C for connection to the associated components of the revascularization system (not shown). A central passageway 20D extends through the catheter and terminates at an open free end 20E (FIGS. 7 and 1). In the exemplary embodiment of catheter 20, the passageway 20D is arranged to carry an infusate liquid therethrough for ejection via opening 20E into the portion of the vessel being revascularized or diagnosed.

Turning now to FIG. 1 the details of the connector 22 will now be considered. As can be seen the connector is in the form of a helical channel 28 cut into the wall 30 of the catheter at the distal end portion 20B so that it is in communication with the interior passageway 20D of the catheter along the entire length of the channel. The channel 28 may be of fixed or variable pitch and includes a widened or flared mouth 32 where it meets or merges with the open free end 20D of the catheter. It is through this mouth that the guide-wire, catheter or other elongated guide member is inserted into the channel. The opposing sides of said mouth 32 may be radially offset or displaced (not shown), relative to each other, to facilitate the entry of said guide-wire 24 into said channel 28. The proximal end of the channel 28 terminates in an elongated slot or exit window 34 that is also in communication with the interior passageway 20D. It is through the window 34 that the guide-wire exits the channel. Thus, the channel forms a path into which the guide-wire can be inserted to slidingly connect the catheter to the guide-wire. As will be discussed in detail to follow, the path is constructed so that the entry of the guide-wire into and through it can be facilitated easily, quickly and reliably with only a slight twisting action. It should be understood that the connector segment of catheter 20 can be a stand-alone device which may be positioned or otherwise attached to a portion (e.g. the distal tip) of any catheter or elongated member. For example, the sleeve-like tubular connector system can be provided in a number of diameters and lengths and can be slide onto the end of a variety of compatible catheters or elongate members and then secured in place (e.g. crimped).

In accordance with one preferred aspect of this invention the material making up the connector portion of catheter 20 is preferably resilient so that the guide-wire 24 can be extended into the mouth 32 of the channel and then into contiguous portion of the channel 28, whereupon the channel flexes open somewhat to enable the guide-wire to pass therethrough to exit from the window 34. As the guide-wire moves proximally along the channel to the window 34, portions for the channel distally of the guide-wire flexes back to the initial position, whereupon when the guide-wire is within the window, the channel will have assumed its unflexed or normally closed condition. It should, however, be pointed out at this juncture that the catheter or the material forming slot need not be resilient, so long as the slot can accommodate the guide-wire therein to enable it to slide with respect thereto, as will be described later.

Figure 2:
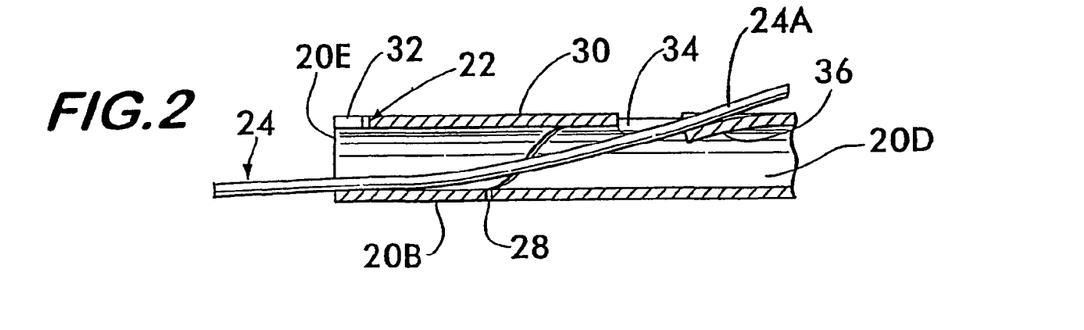
FIG. 2 is a longitudinal sectional view of the distal end of the embodiment of the catheter shown in FIG. 1.

In order to facilitate the exit of the guide-wire 24 from the channel 28 at the window 34 and to ensure that the guide-wire extends closely parallel to the outer surface of the catheter from its exit point proximally, an elongate recess or depression 36 is formed in the wall 30 of the catheter 20 immediately proximally of the window 34. The recess 36 extends along an axis parallel to the longitudinal axis of the catheter and, as best seen in FIG. 2, inclines upward from its lowest point where it merges with the proximal end of the window 34 to the point where it terminates at the outer circular surface of the catheter proximally of the window.

In the exemplary embodiment shown the outer diameter of the catheter is approximately 0.05 inch. The spiral channel 20 forms at least one complete revolution about the periphery of the catheter so that the entry mouth 32 is axially aligned with the exit window 34. The width of the entrance mouth is approximately 0.025 inch. The width of the exit window is greater than the width of the channel 28, e.g., 0.02 inch versus 0 to 0.015_inch. The length of the channel 28 measured longitudinally from the open end 20E of the catheter to the proximal end of the window 34 (i.e., the lowest point of the recess 36) is approximately 0.25 inch. It should be understood that in some instances it may be desirable that the open end 20E of the connector portion of the catheter be beveled or tapered to provide a good fit and smooth transition when the catheter is advanced along to the guide-wire through tissue or the vasculature of the living being.

In order to enable the user of the catheter to orient it in the desired rotational attitude for mounting onto the guide-wire, a process to be discussed in detail later, an indicator marker or indicia, such as an arrow 38, is provided on the catheter aligned with the flared mouth 32 so that the user of the catheter can readily determine the location of the channel's mouth 32 by viewing the indicator arrow 38.

Figure 10:
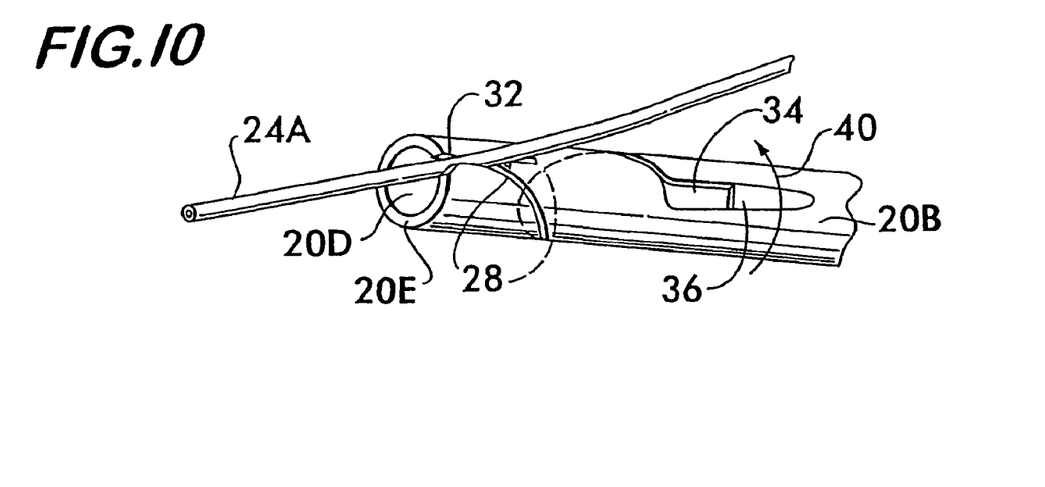
FIG. 10 is an isometric view similar to FIG. 9 but showing the distal end of the embodiment of the catheter of FIG. 1 during an intermediate step in the mounting of the catheter on the guide-wire.
Figure 11:
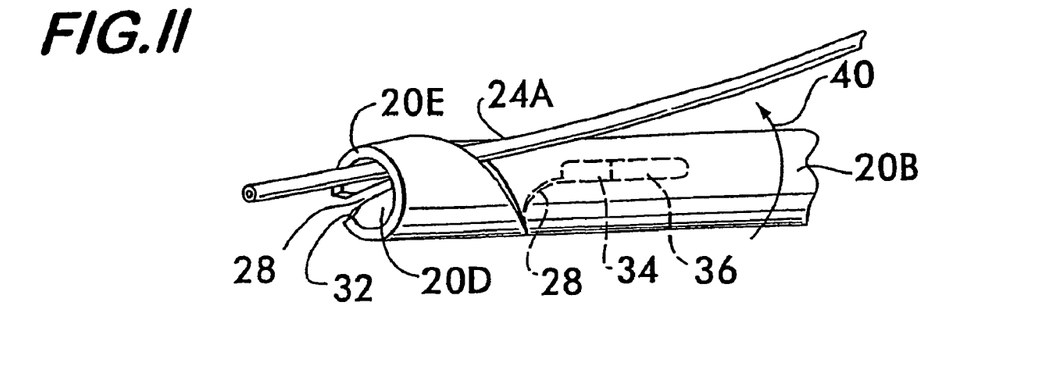
FIG. 11 is an isometric view similar to FIGS. 9 and 10 but showing the distal end of the embodiment of the catheter of FIG. 1 at a still later step in the mounting of the catheter on the guide-wire.

The mounting of the catheter 20 on the guide-wire 24 will now be discussed with reference to FIGS. 9-11. It is assumed that the guide-wire is already in place so that its distal end (not shown) is located at some internal situs within the body of the being, while its proximal end is located outside the body of the being, with some intermediate portion, designated by the reference number 24A herein, also being located outside the body of the being distally of the proximal end of the guide-wire. It is at this intermediate position that the catheter 20 is mounted on the guide-wire using the connector 22. It should be pointed out at this juncture that while the portion 24A of the guide-wire is preferably outside the body of the being, such an arrangement is not required. In this regard in some medical applications the guide-wire portion 24A where the catheter is to be connected may be located internally of the being and access provided to it via a natural body orifice or opening or through some surgically formed opening.

Figure 9:
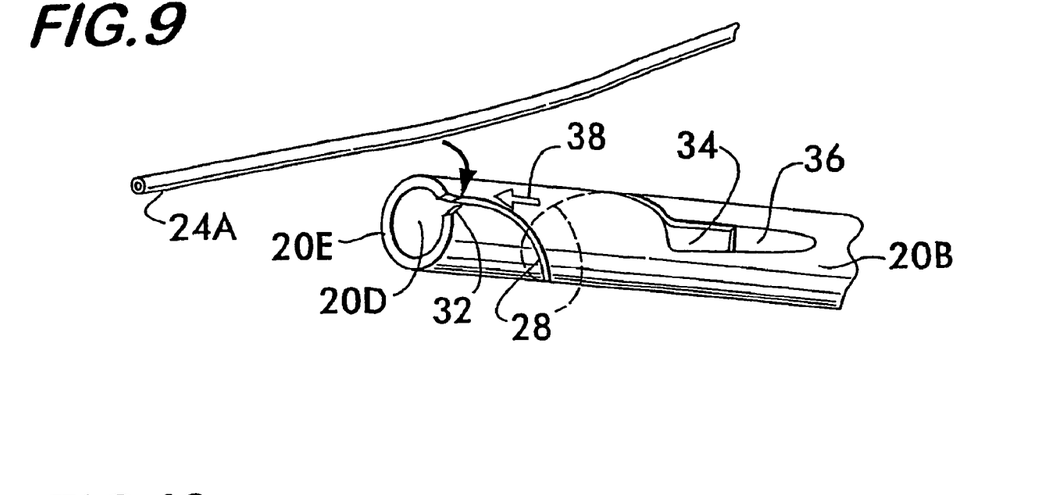
FIG. 9 is an isometric view of the distal end of the embodiment of the catheter shown in FIG. 1 during an initial step in the mounting of the catheter on the guide-wire.

In any case, as best seen in FIG. 9 the catheter 20 is oriented or twisted so that the entry mouth 32 at the distal end of the channel is aligned with the portion 24A of the guide-wire 24. The arrow indicia 38 facilitates the correct orientation alignment procedure. Once aligned the distal end of the catheter 20 is moved in a lateral direction (e.g., from the side of the guide-wire) toward it (or the guide-wire is moved toward the catheter) so that the guide-wire portion 24A enters into the mouth of the channel 116. Then the catheter is twisted or rotated in the direction shown by arrow 40 to cause the guide-wire portion 24A to enter into the contiguous portion of the channel 28, whereupon the channel flexes open, as described earlier. Continued twisting of the catheter in the direction of arrow 40 causes the guide-wire to move further down the channel as shown in FIG. 11. Continued twisting of the catheter with respect to the guide-wire in the direction of arrow 40 eventually brings the guide-wire portion 24A into the exit window 32, as shown in FIGS. 1 and 2, whereupon the guide-wire portion 24 exits the window and is guided upward by the inclined recess 36 until it is generally parallel to the outer surface of the catheter 20 (as best seen in FIG. 1). Once this has been accomplished, the catheter can be slid or moved in the distal direction along the guide-wire to bring the open distal end 20E of the catheter to the desired position within the being's body, e.g., at a situs of the atherosclerotic deposit to be removed.

Figure 3:
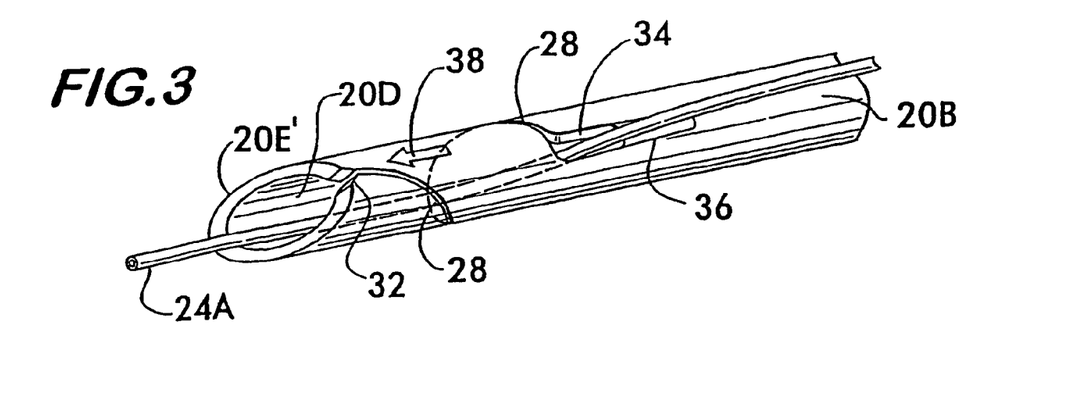
FIG. 3 is an isometric view of the distal end of another embodiment of a catheter, e.g., a beveled distal end catheter, constructed in accordance with this invention and shown after it has been mounted on a conventional guide-wire by a "helical-cut" connector forming a portion of the distal end of the catheter.
Figure 4:
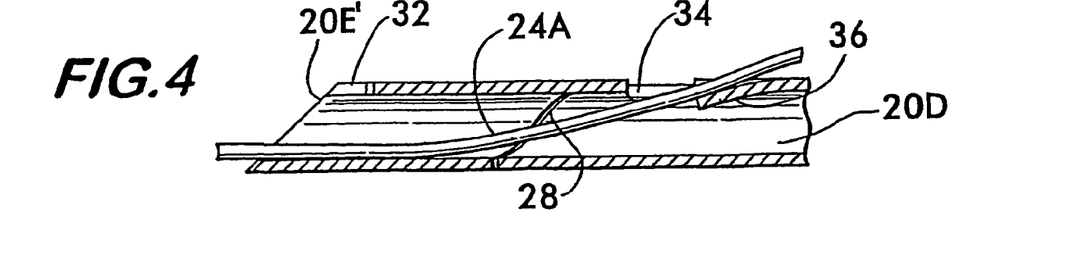
FIG. 4 is a longitudinal sectional view of the distal end of the embodiment of the catheter shown in FIG. 3.

In FIGS. 3 and 4 there is shown an alternative embodiment of a catheter 20' constructed in accordance with this invention. The catheter 20' is in all material respects identical to the catheter 20, except for the shape of its distal end. Thus, in the interest of brevity the details of the construction and the operation of the catheter 20' will not be reiterated and the same reference numbers will be given to the common components. As can be seen in FIGS. 3 and 4 the distal end of the catheter 20' includes a beveled end 20E'. The entry mouth to the channel 28 is located on the most proximal portion of the beveled end 20E' for initial receipt of the guide-wire portion 24A therein.

Figure 5:
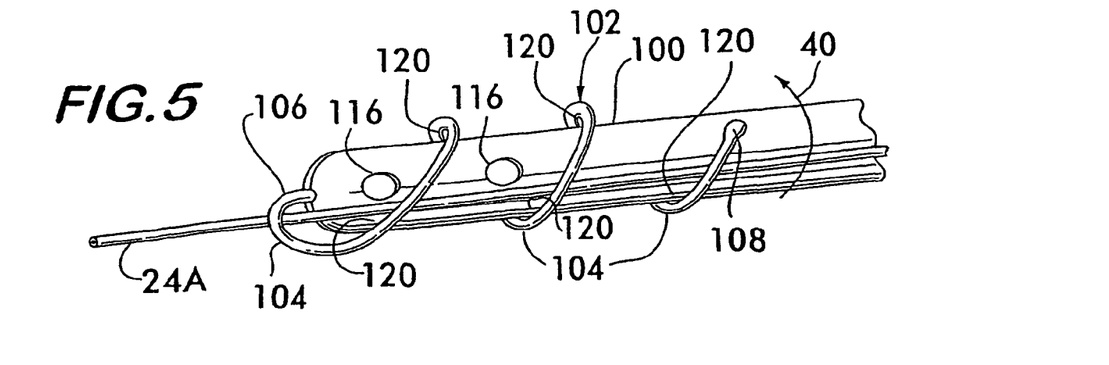
FIG. 5 is an isometric view of the distal end of still another embodiment of a lo catheter constructed in accordance with this invention and shown after it has been mounted on a conventional guide-wire by a "pigtail" connector forming a portion of the distal end of the catheter.
Figure 6:
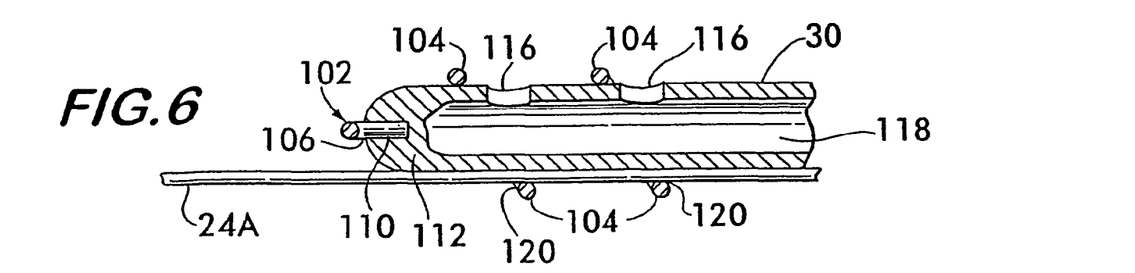
FIG. 6 is a longitudinal sectional view of the distal end of the embodiment of the catheter shown in FIG. 5.

In FIGS. 5 and 6 there is shown another embodiment of a catheter 100 constructed in accordance with this invention. The catheter 100 also includes a connector 102 (to be described in detail hereinafter) for facilitating the mounting of the catheter on a portion 24A of the guide-wire from a lateral or side direction and without requiring access to either end of the guide-wire. However, unlike the embodiments of FIGS. 1-4, the connector 102 of the catheter 100 is located externally to the outer surface of the distal end of the catheter 100 to form the path or channel for the guide-wire therebetween.

The connector 102 basically comprises a helical wire having plural consecutive helices 104 and terminating at one end in a distal end portion 106 and at the opposite or proximal end portion 108. The distal end portion 106 is linear and is centrally disposed within the helices 104 (See FIG. 6). The distal end portion is arranged to be fixedly secured in a central bore 110 in the distal end of the catheter 100. As can be seen the distal end of the catheter is closed, e.g., it includes a dome-shaped end wall 112 into which the bore 110 extends. Since the end of the catheter 100 is closed, if it is to be used as an infusating device it includes plural outlet ports or openings 116 extending through the sidewall 30 of the distal end portion and in communication with the central passageway 118 of the catheter. The helices 104 extend backward from the distal end portion 106 of the connector 102 and about the periphery of the outer surface of the catheter 100 to form an annular space or channel 120 therebetween. The thickness of the channel is just slightly greater than the outside diameter of the guide-wire (for reasons to be explained later). The proximal end portion 108 terminates in a somewhat bulbous free end 122 which is also spaced from the outer surface of the catheter and which forms the entry mouth for the channel 120. The connector 102 may be formed of any suitable biocompatible material, e.g., stainless steel, plastic, etc.

The mounting of the catheter 100 on the guide-wire portion 24A is accomplished by orienting or aligning the catheter 100 so that the guide-wire portion can be inserted into the entry mouth, i.e., the space between the bulbous distal free end 122 of the connector 102 and the outer surface of the catheter 100. Once aligned the distal end of the catheter 100 is moved in a lateral direction (e.g., from the side of the guide-wire) toward it (or the guide-wire is moved toward the catheter) so that the guide-wire portion 24A enters into the mouth of the channel 120. Then the catheter 100 is twisted or rotated in the direction shown by arrow 40 to cause the guide-wire portion 24A to enter into the contiguous portion of the channel 120, i.e., the helical portion defined by the helix closest to the free end 122. Continued twisting of the catheter in the direction of arrow 40 causes the guide-wire to move further down the channel, guided by the helices 104 until it exits from the channel at the distal most helix 104. At this time the guide-wire will be within the confines of the channel and disposed parallel to and very closely adjacent to the outer surface of the catheter. Once this has been accomplished, the catheter 100 can be slid or moved in the distal direction along the guide-wire 24 to bring the distal end of the catheter to the desired position within the being's body, e.g., at a situs of the atherosclerotic deposit to be removed.

In accordance with one preferred aspect of this invention the diameter of the wire making up the connector 102 is quite small, e.g., 0.010 inch, and the thickness of spacing between the inner surfaces of the connector's helices 102 and the outer surface of the catheter 100 (i.e., the thickness of the annular channel 120) is just slightly larger than the outside diameter of the catheter. Thus, the catheter 100 with the connector 102 thereon will still exhibit a small crossing diameter (albeit somewhat greater than a comparable diametrically sized catheter making use of the connectors like shown in FIGS. 1-4).

Figure 12:
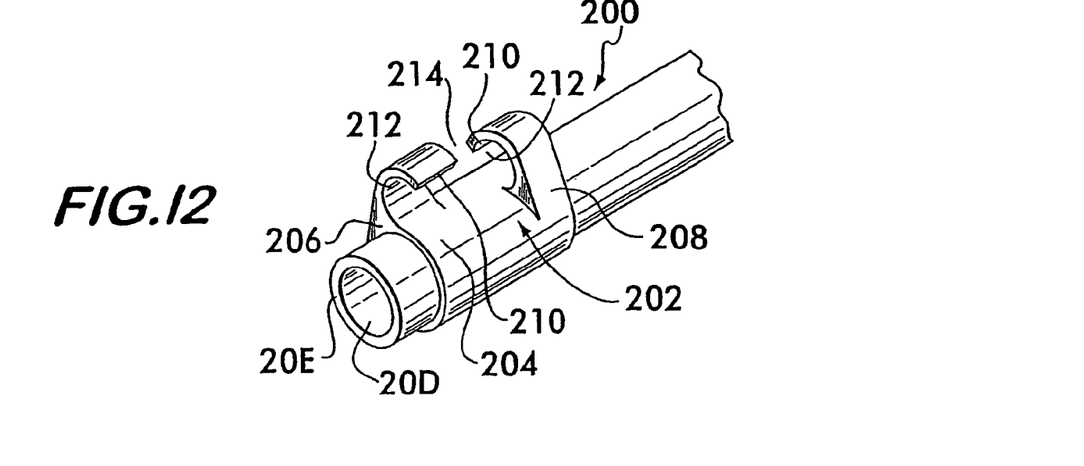
FIG. 12 is an isometric view of the distal end of another embodiment of a catheter constructed in accordance with this invention.
Figure 13:
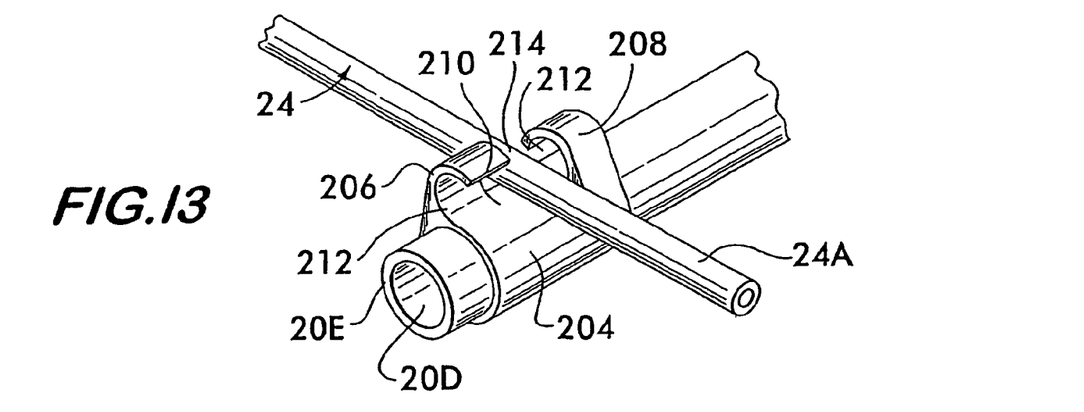
FIG. 13 is an isometric view similar to FIG. 12 but showing the distal end of the embodiment of the catheter of FIG. 12 during an initial step in the mounting of the catheter on a guide-wire.
Figure 14:
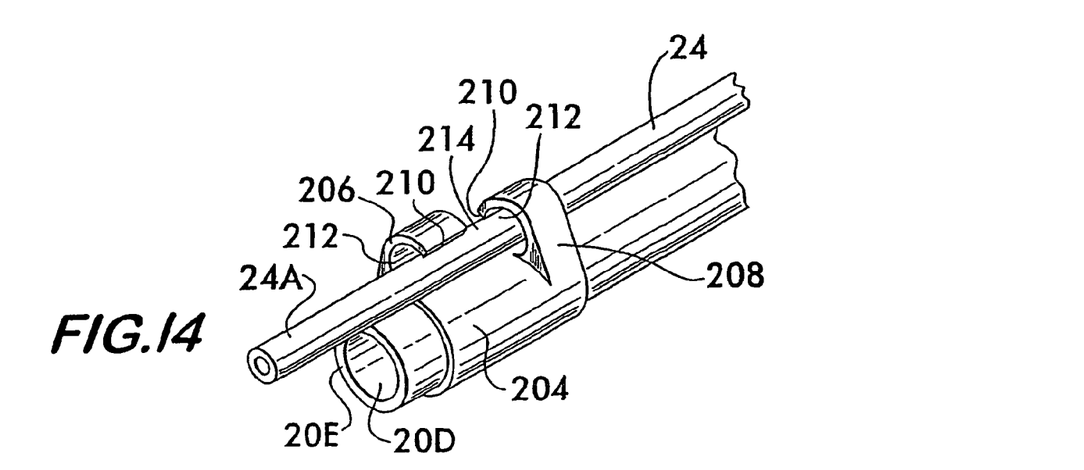
FIG. 14 is an isometric view similar to FIGS. 12 and 13 but showing the distal end of the embodiment of the catheter of FIG. 12 after the catheter has been mounted on the catheter on the guide-wire.

In FIGS. 12-14 there is shown yet another alternative embodiment of a catheter 200 constructed in accordance with this invention. The catheter 200 is similar to the catheter 20 in that it is a hollow tubular member having a central passageway 20D terminating at an open distal end 20E, yet is also similar to the catheter 100 in that catheter 200 includes an externally located connector 202. The connector 202 is like the other connectors described heretofore arranged to enable a guide-wire 24 or other elongated guide member to be readily connected to the catheter by inserting it into a path (to be described hereinafter) by a twisting action, whereupon the catheter or other instrument can be slid along the guide-wire or other elongated guide member, yet is resistant to accidental disconnection.

As can be seen the connector 202 basically comprises a sleeve 204 formed of any biocompatible material, like those described heretofore, and having a pair of fingers 206 and 208 projecting outward therefrom. The sleeve 204 includes a circular central passageway whose inside diameter is approximately the same as the outside diameter of the distal end portion of the catheter 200 to accommodate that portion of the catheter extending therethrough. The sleeve is secured in place by any suitable means, e.g., an adhesive, by friction fit, etc. Moreover, the sleeve may be integrally formed on the distal end portion of the catheter. In fact, as will be appreciated from the discussion to follow, the use of a sleeve may be eliminated if the connector is formed integrally with the catheter. In such an arrangement, all that is required is that distal end of the catheter include the fingers 206 and 208 to form the guide-wire receiving path.

Each of the fingers 206 and 208 projects outward from the longitudinal axis of the connector and the longitudinal axis of the distal end of the catheter 200. Each of the fingers includes an overhanging, e.g., arcuate, free end 210. The free end of the respective fingers are directed in opposed directions to each other, i.e., they are directed so that they face each other but are offset from each other in the longitudinal direction. In particular, the free end 210 of the finger 206 is directed from one side of the catheter 200 towards the free end 210 of the finger 208 on the other side of the catheter. The fingers 206 and 208 may extend tangentially, radially or at some other orientation away from the central longitudinal axis of the catheter 200 so that the free end 210 of the finger 206 and the free end 210 of the finger 208 each form a respective portion of a channel or path 212 between them and the portion of the sleeve from which they project (or from the portion of the catheter from which they project if no sleeve is utilized, e.g., the fingers are formed integrally with the catheter 200).

In the preferred embodiment shown herein the path 212 is of a generally circular cross-section and extends linearly along the longitudinal axis of the catheter immediately adjacent the outer surface of the sleeve 204. It is in this channel or path 214 that the guide-wire portion 24A of the guide-wire 24 is arranged to be inserted to slidingly mount the catheter on the guide-wire. In accordance with a preferred embodiment of this invention the free ends 210 of the fingers 206 and 208 extend around the periphery of the guide-wire so that the fingers and contiguous portion of the sleeve each engage or encircle more than 180 degrees of the periphery of the guide-wire when the guide-wire is within the path or channel to prevent the guide-wire from accidentally coming out of the path or channel. The entry point or entrance to the path or channel 212 is provided by the space or gap 214 between the fingers 206 and 208.

In order to minimize the crossing-diameter of the catheter 200, the fingers 206 and 208 of the connector are preferably dimensioned to keep their height or projection from the central longitudinal axis of the catheter 200 as short as possible, while still enabling the guide-wire portion 24A to be held securely in the path 212 for sliding movement resistant to accidental disconnection. Thus, in the preferred embodiment shown in the cross-sectional area of the channel 212 is just slightly larger than the outside diameter of the guide-wire 24A and the fingers are very thin.

The connection of the catheter 200 to the guide-wire portion 24A will now be described with reference to FIGS. 13 and 14. As before, it is assumed that the guide-wire 24 is already in place so that its distal end (not shown) is located at some internal situs within the body of the being, while its proximal end is located outside the body of the being, with the intermediate portion 24A of the guide-wire also being located outside the body of the being distally of the proximal end of the guide-wire. As pointed out earlier while the portion 24A of the guide-wire is preferably outside the body of the being, such an arrangement is not required. In this regard in some medical applications the guide-wire portion 24A where the catheter is to be connected may be located internally of the being and access provided to it via a natural body orifice or opening or through some surgically formed opening.

In any case, as best seen in FIG. 13 the catheter 200 is oriented so that the entry mouth or gap 214 of the path 212 at the distal end of the channel is aligned with the portion 24A of the guide-wire 24, e.g., the longitudinal axis of the guide-wire portion 24A is perpendicular to the longitudinal axis of the catheter 200 and is between the fingers forming the gap. Once so aligned the distal end 20E of the catheter 200 is twisted about an axis perpendicular to the longitudinal axis of the catheter to bring the more distally located portion of the guide-wire portion 24A into the path 212 under the finger 206, while at the same time bringing the more proximally located portion of the guide-wire portion 24A into the path 212 under the finger 208 as shown in FIG. 14. This action completes the sliding securement of the catheter on the guide-wire 24. Therefore, once the sliding securement has been accomplished, the catheter 200 can be slid or moved in the distal direction along the guide-wire 24 to bring the open distal end 20E of the catheter to the desired position within the being's body, e.g., at a situs of the atherosclerotic deposit to be removed.

It should be pointed out at this juncture that while the foregoing discussion has described the twisting of the catheter or other tubular instrument with respect to the guide-wire or other elongated guide member to releasably secure the two together, that methodology is not the only method for achieving their releasably securement. Thus, as will be appreciated by those skilled in the art, the guide-wire or other elongated guide member can be twisted with respect to the catheter or other tubular instrument to cause the guide-wire or other tubular instrument to be introduced into the path for holding the two together.

It should also be pointed out that while the foregoing discussion has described catheters or other tubular instruments with the various types of connectors forming a portion thereof, it should be clear that connectors, per se, may be constructed in accordance with this invention for mounting, e.g., retrofitting, to existing catheters or other tubular instruments. Thus, the subject invention not only contemplates catheters or other elongated tubular instruments including connectors for connecting the catheters or other tubular instruments to guide-wires or other elongated guide member, but also contemplates connectors, per se, for use with conventional catheters to achieve those ends.

Figure 15:
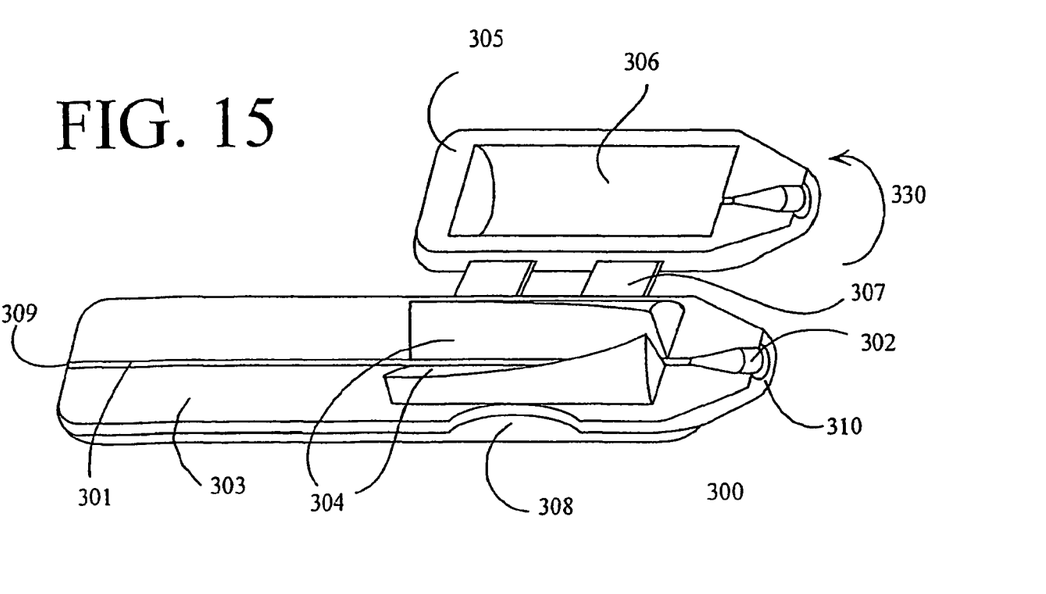
FIG. 15 is an isometric view of the open clamshell attachment tool showing the internal bore and features used to direct the guide-wire into the internal bore prior to the closing of the clamshell.

In a preferred embodiment an attachment tool 300 comprises a hinged clamshell construction, that when closed provides for an interior longitudinal bore 301 for the guide-wire (or other elongated guide member) that expands into a conical funnel portion 302 at the leading end (proximal end) 310 of the tool. The tool further comprises two halves, a first half 303 on which is located on a pair of raised v-shape protrusions 304 through which the guide-wire 24 is placed into the bore 301. The raised protrusions 304 are arranged co-linear with a bore 301, and on either side of same, to allow for easy placement of said guide-wire, and also engage the second half of the tool 305 in a mating depressed portion 306. The engagement of the protrusion of the first half and the depression of the second half, during closing of the tool 300 by rotating 330 one half of tool, serve to align the closed tool, thereby creating a smooth funnel opening 302, or catheter entry port. Living hinges 307 allow for one-handed closure of the tool around the guide-wire 24 (not shown), a small indentation 308 provides for a tab to open the closed tool to remove it from the attached catheter-guide-wire apparatus. The bore 301 extends the full length of the first half 303, and can be utilized for guide-wire alignment at the distal end 309 opposite the funnel opening 302.

Figure 16:
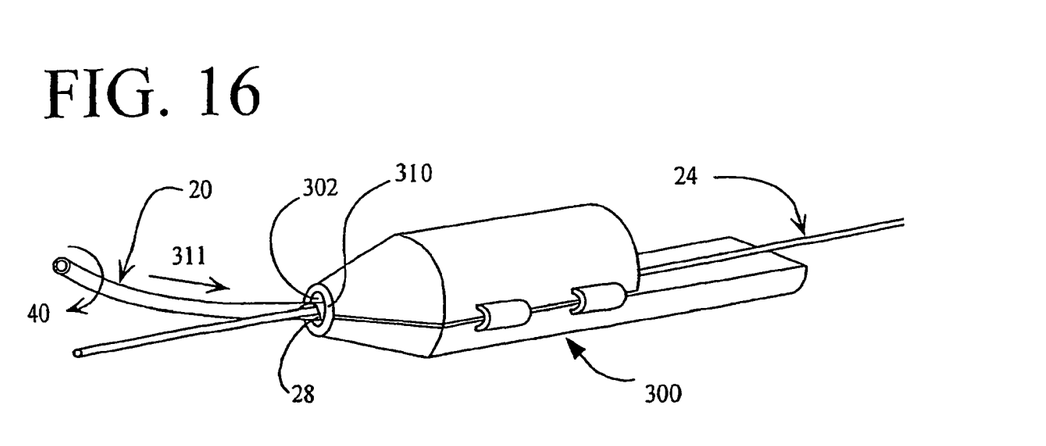
FIG. 16 is an isometric view of the catheter attached to the guide-wire inside the funnel of the closed attachment tool.

The tool 300 is intended to be closed over the guide-wire 24, as is shown in FIG. 16, whereby the guide-wire shall then reside within the bore 301 inside the closed tool. The catheter 20 containing the distal tip connector 28 (e.g., one of the various embodiments previously described) is then advanced into the open funnel portion of the tool 302, and the catheter is simultaneously advanced 311 and twisted 40 to effect attachment of the connector 310 to the guide-wire (as previously described). The conical funnel 302 serves to press the catheter against the guide-wire, facilitating the entry of the guide-wire into the mouth 32 provided at the entry of the helical channel 28.

In yet another embodiment, the attachment tool 300 causes alignment of the guide-wire 24 and the catheter 20, as shown in FIG. 16; however, the tool of this embodiment further utilizes a detent to facilitate engagement of the guide-wire 24 with the channel 28. The detent comprises a mouth 32 (as shown in FIG. 1) or an offset (not shown), as previously described herein.

Once the catheter is fully attached, the tool is then opened with tab 308 to release the guide-wire, and the catheter can be advanced or retracted freely and securely along the wire. This exemplary tool embodiment is designed to be functional and easy-to-use with one hand, but other embodiments causing contact and engagement of the catheter and wire are anticipated and within the concept of the present invention.

The attachment tool 300 may be sized to allow its insertion into a natural body orifice, or other surgical created entry site, wherein the tool may attach a plurality of catheters while the tool is located entirely inside of the body. It is within the concept of this invention to operate the attachment tool with hands, fingers, or other instruments, thereby enabling the attachment of catheters to a guide-wire at various remote areas within the body.

The longitudinal bore 301 extends between the proximal and distal ends of the tool 300 and allows communication through the tool. This communication allows catheters or other instruments comprising functional members (not shown) located distal to the distal tip connector, and attached thereto, to be arranged in the bore 301 such that the member extends through the distal end 309 of said tool 300. As a non-limiting example, the functional member may comprise a steering tip (for steering the functional member, and catheter, independently of the guide-wire 24), an angioplasty balloon (with or without a steering tip, which may be used to occlude an arterial branch), or a catheter for the delivery of a therapy or diagnostic agent or device (e.g., a drug, biologically active agent, radioactive source, ultrasonic source, or other prosthesis).

Since the distal tip connector, as previously described, does not need access to the ends of the guide-wire, a plurality of catheters may be attached to the guide-wire while the guide-wire is in-place (i.e., extending into the body, to the site of the procedures) without requiring access to the end of the guide-wire. A preferred embodiment of the attachment tool, of the present invention, facilitates this attachment.

Figures 17, 17A:
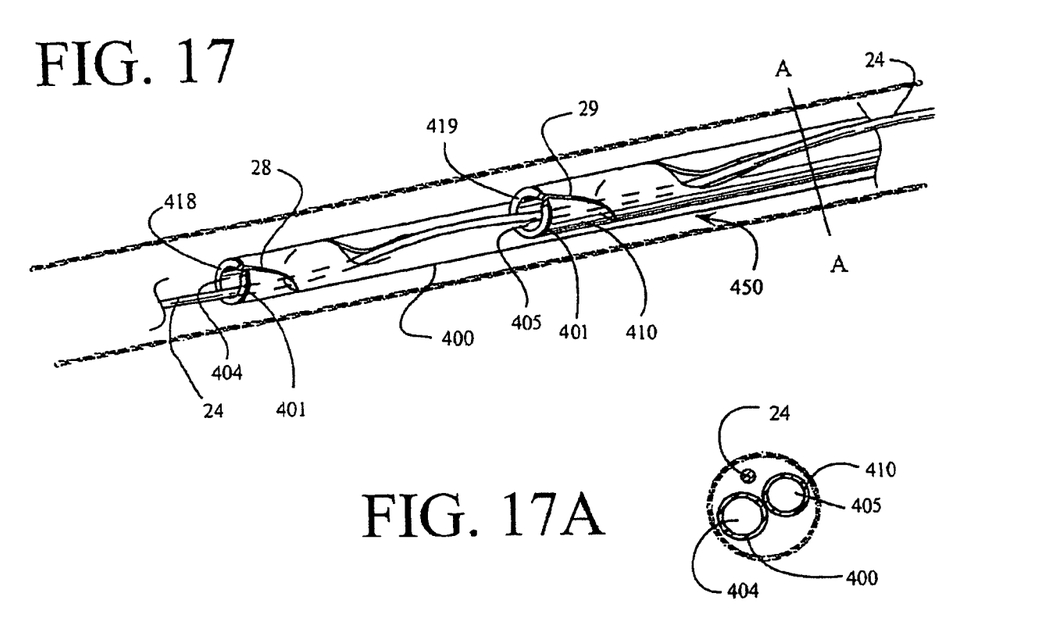
FIG. 17 is an isometric view of a system including a guide-wire having a plurality of catheters connected thereon, with each catheter have a distal tip connector connected to the guide-wire by the attachment tool of FIG. 15.
FIG. 17A is a cross-sectional view of the embodiment of the catheter system shown in FIG. 17, at section line A-A.

As an example, FIG. 17 shows a system 450 composed of a pair of catheters 400 and 410, each including a channel-type of distal tip connector. In particular, catheter 400 includes distal tip connector 28, while the catheter 410 includes a distal tip connector 29. The connector 29 is identical to connector 28 described heretofore and shown in more detail in FIG. 1. The catheters 400 and 410 may each additionally include a radio-opaque marker 401 to facilitate the precise placement of the catheter during any intravascular procedure utilizing the catheter. The catheter 410 is attached to the guidewire 24 in a similar manner to catheter 400 but located proximally to the distal end of the catheter 400. The attachment tool 300 (shown clearly in FIGS. 15-16) effects the placement of the catheters 400 and 410 of the multiple catheter system 450. It should be appreciated by those skilled in the art that the system 450 may include more than the two catheters shown, with the number of catheters actually being placed on the guide-wire limited only by the crossing diameter of the artery or other blood vessel into which they are placed.

The benefits of the attachment tool 300 and the multiple catheter system constructed in accordance with this invention can be readily appreciated by reference to FIGS. 17, 17A, 18 and 18A. In particular, the cross-sectional view of FIG. 17A shows the non-concentric arrangement of the catheters 400 and 410 and guidewire 24 of the system 450 in a blood vessel. As previously described, the flow or access through each of the catheters of the system is not impeded by he guide-wire since neither catheter 400 nor catheter 410 needs to house other catheters or the guide-wire extending fully therethrough, i.e., only the distal end portion of each catheter houses a portion of the guide-wire. The guidewire 24 is effectively located external to each catheter, except for the portion at the respective connectors 28 and 29, that is, the portion contiguous with the distal ends 418 and 419, respectively. Thus, it can be seen that the flow path, i.e., the interior passageway 404, through the first catheter remains largely unrestricted by the guidewire. In a similar manner, the flow path or passageway 415 through the catheter 410 also remains unrestricted by the guidewire.

As will be appreciated by those skilled in the art, the free flow of fluid through the catheters of the system 450 allows or improves the ability to perfuse diagnostic or therapeutic fluids and drugs via the interior of its catheters. Additionally, higher pressures and/or flow rates can be accommodated by the system 450 to facilitate the removal of fluids and/or debris from within the blood vessel.

Figure 18:
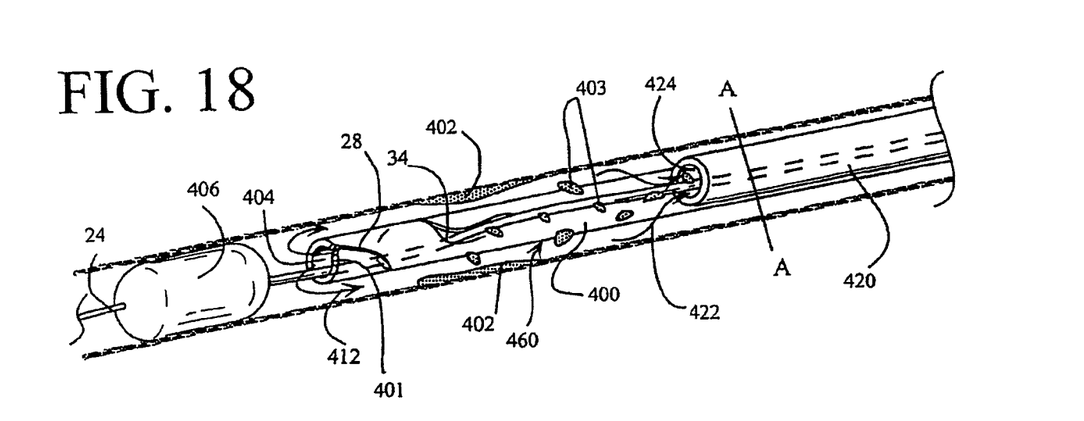
FIG. 18 is an isometric view of a system including a guide-wire having a plurality of catheters connected thereon, with a first catheter having a distal tip connector connected to the guide-wire by use of the attachment tool of FIG. 15 and a second catheter loaded onto the guide-wire in a traditional manner from the end of the guide-wire.

In FIG. 18 there is shown a system 460 including a pair of catheters 400 and 420 on a single guidewire 24. The catheter 400 is constructed like that of FIG. 17. The catheter 420 is conventional type and is attached to the guidewire 24 proximally of the catheter 400. In particular, the catheter 400 is attached to the guidewire 24 via a distal tip connector 28 like that described above. The second catheter 420, being of a more conventional design, is threaded over the guidewire 24 using the traditional concentric loading configuration or method.

Figure 18A:
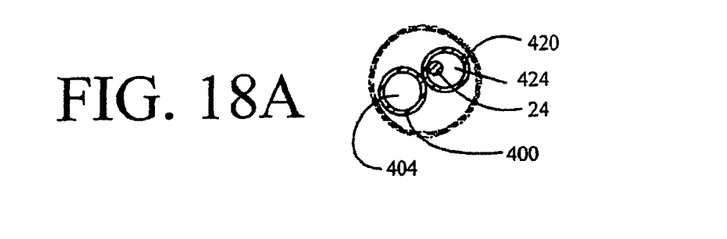
FIG. 18A is a cross-sectional view of the embodiment of the catheter system shown in FIG. 18, at section line A-A.

The concentric loading method inherently restricts the flow of fluid through the hollow interior 424 of the catheter 420 since the guidewire extends through the catheter. Thus, as can be seen in FIG. 18A, the catheter 420 which is loaded over the guidewire 420 in the traditional manner will have a reduced flow path 424 therethrough compared to the flow path of 404 through the catheter 400.

In FIG. 18 the system 460 is shown during the procedure of revascularizing an artery having an atherosclerotic plaque deposit 402 therein. The system shown in FIG. 18 includes a distal balloon 406 on the distal end of the guidewire 24 to provide protection from debris 403 produced during the revascularization procedure flowing distally from the situs of the procedure, which action could cause stroke, heart attack, an adverse pulmonary event or some other adverse effect. The revascularization procedure in the artery may be accomplished by using an infusate fluid which flows down the interior passageway 404 of the catheter 400 and out its open distal end. This flow of infusion liquid out of the catheter 400 to engage the plaque deposit 402 is shown by the arrows 412 in FIG. 18. In carrying out the revascularization procedure infusion fluid may pick up debris 403 liberated from the plaque deposit 402. The fluid flow 412 emanating from the distal opening of the catheter 400 for carrying the debris may be complemented by an additional fluid flow path 34 emanating from the proximal end or window 34 of the distal tip connector 28. In any case, the debris 403 produced during the revascularization is carried via a debris removal flow stream 422 into the open distal end of the passageway 424 in the catheter 420 and from there through the catheter for extraction outside the body of the being.

Figure 19:
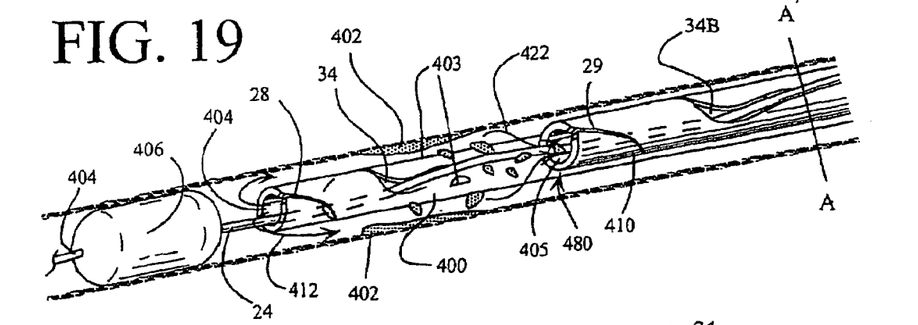
FIG. 19 is an isometric view of a system including a guide-wire having a plurality of catheters connected thereon, with each catheter having a distal tip connector like that of FIG. 17, but with the guide-wire including a debris blocking balloon.
Figure 19A:
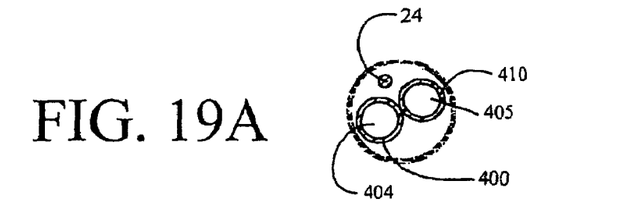
FIG. 19A is a cross-sectional view of the embodiment of the catheter system shown in FIG. 19, at section line A-A.

It should be pointed out at this juncture that the embodiment of the system shown in FIG. 18 is merely exemplary of the benefits of utilizing a multiple catheter system on a single guide-wire. It should be recognized that the system of FIG. 18 may not be as efficient as a system employing multiple non-concentric catheters, such as the system 450 shown in FIG. 17 used with a debris blocking balloon 406. Notwithstanding that fact, the system of FIG. 18 still has considerable utility. However, it is preferable when utilizing a multiple catheter system to utilize catheters constructed like the catheters 400 and 410 of FIG. 17, whose deployment is facilitated by the use of the attachment tool 300 of the present invention. In such an arrangement, best seen in FIG. 19, the system 480 includes debris blocking member or balloon 406 shown attached to the distal end of the guidewire 24. The catheters 400 and 410 are connected to the guide-wire in the manner as described above and operated in the manner described with respect to FIG. 18. The balloon 406 serves to block the distal flow of debris and to facilitate its safe removal.

Figures 20, 20A:
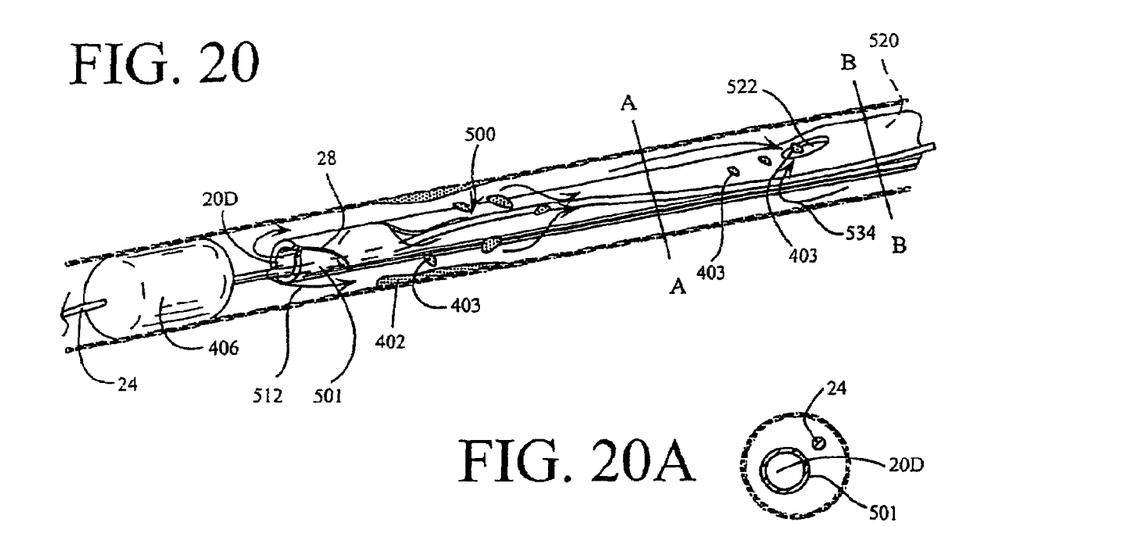
FIG. 20 is an isometric view of a single combination catheter having a plurality of passageways and a distal tip connector, like that of FIG. 17, but with the guide-wire including a debris blocking balloon.
FIG. 20A is a cross-sectional view of the embodiments of the catheter system shown in FIGS. 20 and 21, at section line A-A of FIG. 20.
Figure 20B:
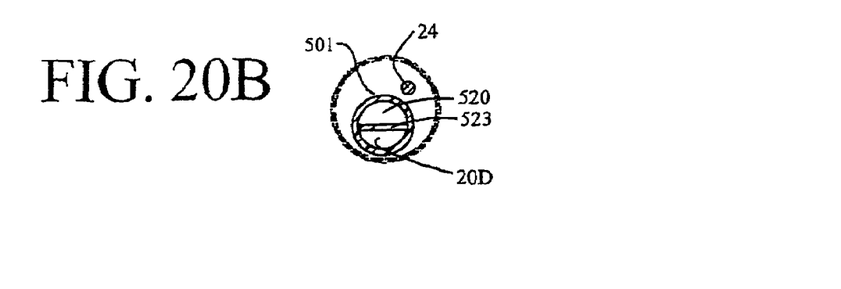
FIG. 20B is a cross-sectional view of the embodiments of the catheter system shown in FIGS. 20 and 21, at section line B-B of FIG. 20.

In yet another embodiment of this invention, there is shown in FIG. 20 a catheter system 500 including a guide-wire 24 and a combination catheter 501. That catheter includes a pair of longitudinal passageways extending through the interior of the catheter. The system shown in FIG. 20 is arranged to present a decreased or minimized cross-sectional area. To that end, the catheter 501 includes a distal end portion having a connector 28 like that shown and described above for attaching the catheter 501 to the guidewire 24. The guidewire 24 has a distally located debris blocking balloon 406. Unlike the catheters 20 and 400 the balance of catheter 501, i.e., the portion from near the distal end to the proximal end (not shown) is of an enlarged outside diameter and is split longitudinally to form a pair of side-by-side passageways which will be described later. An outlet port or hole 522 is located extending through the outer wall of the catheter 501 at the point at which the smaller diameter distal end portion merges with the larger diameter portion. The outlet 522 communicates with a longitudinally extending passageway 520 extending from that opening to the proximal end of the catheter. The passageway 520 is formed by a longitudinally extending wall 523 (see FIG. 20B). The wall 523 extends from the portion at which the outlet 522 is located to the proximal end of the catheter 501. The distal end of the catheter 501 includes a circularly shaped passageway 20D extending from that end proximally. The passageway 20D merges into a semi-circular shaped passageway 20D in the portion of the catheter immediately proximally of the outlet 522. Thus, as shown in FIG. 20B, the portion of the passageway 20D located in the proximal portion of the catheter 501 is of semi-circular shape and is in fluid communication with the circular shaped passageway 20D at the distal end of the catheter 501. The communicating passageways 20D serve to provide a path for introduction of an infusate liquid through the catheter and out of its open distal end. This fluid flowing out of the catheter is shown by the arrows 512. This flow may be used to revascularize the vessel and to carry debris 403 produced by the revascularization procedure to the outlet 522. Thus, the debris can flow into that outlet and through the passageway 520 for removal from the body of the being. The first passageway or channel 20D can be used for carrying drugs or other therapeutic agents along with the infusate fluid into the blood vessel.

Figure 21:
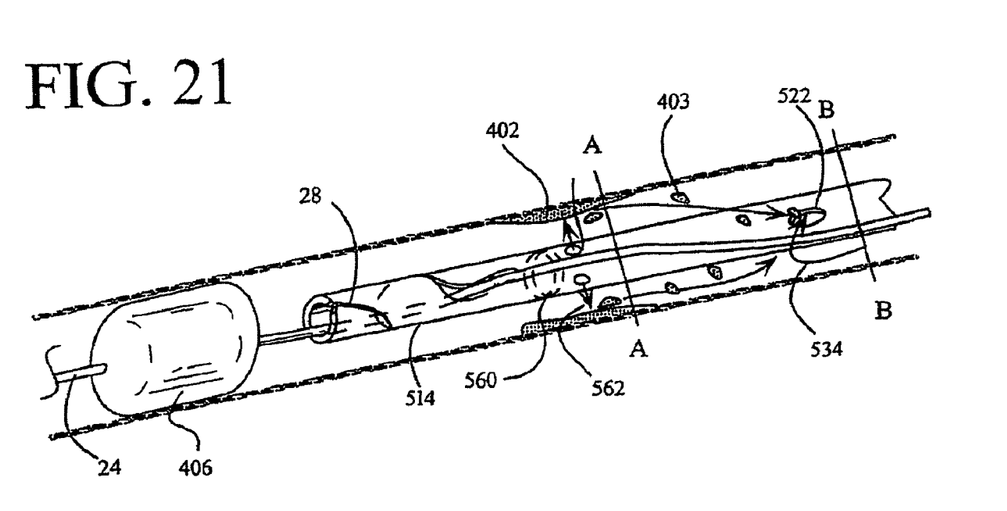
FIG. 21 is an isometric view of a combination catheter, similar to that shown in FIG. 20, but additionally comprises a flow blocking wall and a pair of high-pressure flow ports.

In FIG. 21 there is shown a further embodiment of the system of this invention. The embodiment shown in FIG. 21 comprises a catheter 514 which is similar to the catheter 501 except that it includes a fluid stopping wall 560 located just slightly proximally of the connector 28. A pair of outlet ports 562 are located in the catheter immediately proximally of the fluid stopping wall 560. The outlets 562 are in fluid communication with the infusion fluid passageway 20D (see FIG. 20B). Thus, an infusion fluid flowing down the passageway 20D is blocked from gaining egress out the distal end of the catheter 501, but instead passes through the outlet ports 562 in the form of plural high pressure flows 561. The high pressure flows 561 can be very effective for removing the plaque 402 from the interior of the artery wall. The debris 403 produced by the plaque removal can then flow into the outlet 522 and down its communicating passageway 520 for removal from the body of the being in the same manner as described above.

Thus, it should be appreciated that the high pressure combination catheter 514 of FIG. 21 is particularly useful for, among other things, dislodging debris from the artery or lumen wall or assisting the penetration of the fluid, which may carry a therapeutic agent or drug, into or through the arterial wall or tissue.

It should be pointed out at this juncture that the foregoing multicatheter and combination catheter embodiments described above may utilize an infusate fluid introduced through the first catheter component at a first flow rate and the infusate and debris together with some blood or bodily fluid may be removed at a second flow rate that may be similar to or greater than the first flow rate. A greater second flow rate may cause the removal of some upstream blood or fluid via the path 534 (see FIGS. 20 and 21) to ensure that no debris 403 passes the outlet 522.

Without further elaboration the foregoing will so fully illustrate our invention that others may, by applying current or future knowledge, adopt the same for use under various conditions of service.

The invention claimed is:

1. A tubular instrument system arranged to be used with a guide-wire or other elongated guide member, the guide-wire or other guide member having a distal end portion arranged to be extended to some interior position within a lumen in the body of a living being, the guide-wire or other guide-member having a proximal end portion arranged to be located outside the body of the being, said tubular instrument system comprising at least a first tubular component and a second tubular component, wherein said first tubular component comprises an end portion arranged to be readily connected to the guide-wire or other guide member so that said first tubular component can be guided to a desired position within the body of the being along the guide-wire or other guide member, said end portion of said first tubular component comprising a connector establishing a first path into which a portion of the guide-wire or other guide member can be inserted from a lateral direction by a twisting action without requiring access to either end of the guide-wire or other guide member, said first tubular component arranged to have a fluid introduced therethrough, and wherein said second tubular component comprises an end portion arranged to readily connected to the guide-wire or other guide member so that said second tubular component can be guided to a desired position within the body of the being along the guide-wire or other guide member, said end portion of said second tubular component comprising a connector establishing a second path into which a portion of the guide-wire or other guide member can be inserted from a lateral direction by a twisting action without requiring access to either end of the guide-wire or other guide member, said second tubular component being arranged to evacuate fluid and debris therethrough.

2. The instrument of claim 1 wherein said first tubular component includes a hollow wall portion forming the distal end thereof, said hollow wall terminating at a distal opening, and wherein said first path is a channel formed in said hollow wall portion and communicating with said opening.

3. The instrument of claim 2 wherein said distal end of said channel is in the form of a flared mouth having a width greater than the width of said channel to facilitate the insertion of the guide-wire or other guide member into said channel.

4. The instrument of claim 1 wherein said second tubular component includes a hollow wall portion forming the distal end thereof, said hollow wall terminating at a distal opening, and wherein said second path is a channel formed in said hollow wall portion and communicating with said opening.

5. The instrument of claim 4 wherein said distal end of said channel is in the form of a flared mouth having a width greater than the width of said channel to facilitate the insertion of the guide-wire or other elongated guide member into said channel.

6. The system of claim 1 wherein the guide-wire or other guide member comprises a portion of said system, and wherein said system additionally comprises a debris blocking member.

7. The system of claim 6 wherein said debris blocking member is arranged to be operable distally of said first tubular component and said second tubular component.

8. The system of claim 7 wherein said first component is arranged to have a fluid introduced therethrough at a first flow rate, and wherein said second component is arranged to evacuate fluid and debris therethrough at a second flow rate, and wherein said second flow rate is greater than said first flow rate.

9. The system of claim 1 wherein said fluid comprises a drug or therapy agent.

10. A tubular instrument system arranged to be used with a guide-wire or other elongated guide member, the guide-wire or other guide member having a distal end portion arranged to be extended to some interior position within a lumen in the body of a living being, the guide-wire or other guide member having a proximal end portion arranged to be located outside the body of the being, said tubular instrument system comprising at least a first tubular component and a second tubular component, wherein said first tubular component comprises and end portion arranged to be readily connected to said guide-wire or other guide member so that said first is tubular component can be guided to a desired position within the body of the being along the guide-wire or other guide member, said end portion of said first tubular component comprising a connector at establishing a first path into which a portion of the guide-wire or other guide member can be inserted from a lateral direction by a twisting action without requiring access to either end of the guide-wire or other guide member, said first tubular component arranged to have a fluid introduced therethrough, and wherein said second tubular component comprises a channel portion arranged to readily connect said instrument to the guide-wire or other guide member so that said second tubular component can be guided to a desired position within the body of the being along the guide-wire or other guide member, said second tubular component being arranged to evacuate fluid and debris therethrough.

11. The system of claim 10 wherein said second tubular component comprises a proximal end and a distal end, with said channel extending therebetween.

12. The system of claim 10 wherein the guide-wire or other guide member comprises a portion of said system and wherein said system additionally comprises a debris blocking member.

13. The system of claim 12 wherein said debris blocking member is arranged to be operable distally of said first tubular component and said second tubular component.

14. The system of claim 13 wherein said first component is arranged to have a fluid introduced therethrough at a first flow rate, and wherein said second component is arranged to evacuate fluid and debris therethrough at a second flow rate, and wherein said second flow rate is greater than said first flow rate.

15. The system of claim 10 wherein said fluid comprises a drug or therapy agent.

16. A combination catheter system arranged to be used with a guide-wire or other elongated guide member, the guide-wire or other guide member having a distal end portion arranged to be extended to some interior position within a lumen in the body of a living being, said guide-wire or other guide member having a proximal end portion arranged to be located outside the body of the being, said combination catheter system comprising at least a first tubular component and a second tubular component, wherein said first tubular component comprises an end portion arranged to be readily connected to the guide-wire or other guide member so that said first tubular component can be guided to a desired position within the body of the being along the guide-wire or other guide member, said end portion of said first tubular component comprising a connector establishing a first helical path into which a portion of the guide-wire or other guide member can be inserted from a lateral direction, said first tubular component arranged to have a fluid introduced therethrough, said second tubular component attached adjacent to said first tubular component and having a distal end portion at which a path or opening is located and into which at least a portion of the fluid and debris may enter, said second tubular component being arranged to evacuate fluid and debris therethrough.

17. The system of claim 16 wherein the guide-wire or other guide member comprises a portion of said system and wherein said system additionally comprises a debris blocking member.

18. The system of claim 17 wherein said debris blocking member is arranged to be operable distally of said first tubular component and said second tubular component.

19. The system of claim 18 wherein said first component is arranged to have a fluid introduced therethrough at a first flow rate, and wherein said second component is arranged to evacuate fluid and debris therethrough at a second flow rate, and wherein said second flow rate is greater than said first flow rate.

20. The system of claim 16 wherein said fluid comprises a drug or therapy agent.

21. A combination catheter system arranged to be used with a guide-wire or other elongated guide member, the guide-wire or other guide member having a distal end portion arranged to be extended to some interior position within a lumen in the body of a living being, the guide-wire or other guide member having a proximal end portion arranged to be located outside the body of the being, said combination catheter system comprising at least a first tubular component and a second tubular component, wherein said first tubular component comprises an end portion arranged to be readily connected to the guide-wire or other guide member so that said first tubular component can be guided to a desired position within the body of the being along the guide-wire or other guide member, said end portion of said first tubular component comprising a connector into which a portion of the guide-wire or other guide member can be inserted from a lateral direction with a twisting action, said first tubular component arranged to have fluid injected therethrough, said second tubular component being attached adjacent to said first tubular component and having a distal end portion, said second component having a path or opening at said distal end portion into which at least a portion of the fluid and debris may enter, said second tubular component being arranged to evacuate fluids and debris therethrough.

22. The system of claim 21 wherein the guide-wire or other elongated guide member comprises a portion of said system and wherein said system additionally comprises a debris blocking member.

23. The system of claim 22 wherein said debris blocking member is arranged to be operable distally of said first tubular component and said second tubular component.

24. The system of claim 23 wherein said first component is arranged to have a fluid introduced therethrough at a first flow rate and wherein said second component is arranged to evacuate fluid and debris therethrough at a second flow rate, and wherein said second flow rate is greater than said first flow rate.

25. The system of claim 23 wherein said first tubular component additionally comprises a fluid stopping member and outlet ports, said fluid stopping member being arranged distal to said outlet ports to direct high pressure flow through said ports.

26. The system of claim 21 wherein said fluid comprises a drug or therapy agent.

* * * * *